United States Patent [19]
Mitter

[11] Patent Number: 5,814,726
[45] Date of Patent: Sep. 29, 1998

[54] METHOD FOR DETERMINING THE ABSOLUTE HUMIDITY OF AIR

[75] Inventor: Helmut Mitter, Hellmansödt, Austria

[73] Assignee: E & E Elektronik Gesellschaft M.B.H., Austria

[21] Appl. No.: 816,948

[22] Filed: Mar. 12, 1997

[30] Foreign Application Priority Data

Apr. 10, 1996 [AT] Austria ............................... GM 202/96

[51] Int. Cl.$^6$ ........................... G01N 33/18; G01R 27/22
[52] U.S. Cl. ..................... 73/335.04; 73/29.05; 324/664; 324/689
[58] Field of Search .............................. 73/335.04, 29.05, 73/29.01; 324/664, 689

[56] References Cited

U.S. PATENT DOCUMENTS

| | | | |
|---|---|---|---|
| 5,296,819 | 3/1994 | Kuroiwa et al. | 73/335.04 X |
| 5,531,097 | 7/1996 | Tsuchida et al. | 73/29.01 X |

FOREIGN PATENT DOCUMENTS

| | | | |
|---|---|---|---|
| 3911812 | 10/1990 | Germany. | |
| 19513274 | 11/1995 | Germany. | |
| 2-108952 | 4/1990 | Japan | 73/29.05 |
| 5-209855 | 8/1993 | Japan | 73/29.05 |

OTHER PUBLICATIONS

Sonntag, D., "Formeln verschiedenen Genauigkeitsgrades zur Berechnung des Sättigung s dampfdruckes über Wasser und über Eis und ihre Anwendung auf einige prakitshche Feuchtemessaufgaben," Abhandlungen des Meteorologischen Dienstes Der Deutschen Demokratischen Republik, Nr. 129 (Band XVII), pp. 32–38, 1982.

Sonntag, D., "Important New Values of the Physical Constants of 1986, Vapour Pressure Formulations based on the ITS–90, and Psychrometer Formulae," Z. Meteorol., vol. 70, No. 5, pp. 340–344 (1990).

Hyland, R.W., "A Correlation For The Second Interaction Virial Coefficients and Enhancement Factors for Moist Air" Journal of Research of National Bureau of Standards—A Physics and Chemistry, vol. 79A, No. 4, pp. 551–560, Jul.–Aug. 1975.

*Primary Examiner*—Daniel S. Larkin
*Attorney, Agent, or Firm*—Brinks Hofer Gilson & Lione

[57] ABSTRACT

A method for determining the absolute humidity of air by aid of a capacitive sensor and a temperature sensor as well as a heating element. The sensor temperature is changed upon reaching a predetermined humidity limit value. In order to eliminate the risk of falsified measuring values and to enable long-time stable and accurate measuring also in the high-humidity range, the determination of the humidity of air until reaching the predetermined humidity limit value is effected by evaluating the value measured for the capacity of the sensor. Upon reaching a predetermined limit value, the temperature of the sensor is controlled to a constant sensor capacity by heating and is evaluated.

9 Claims, 4 Drawing Sheets

METHOD FOR DETERMINING THE ABSOLUTE HUMIDITY OF AIR

BACKGROUND OF THE INVENTION

1. Field of the Invention

This invention relates to a method for determining the absolute humidity of air by aid of a capacitive sensor and a temperature sensor as well as a heating element, wherein the sensor temperature is changed upon reaching a predetermined humidity limit value.

The simplest way to determine the absolute humidity of a gas, or of air, is by way of measuring the dew point temperature $T_d$. The dew point temperature is that temperature to which a moist gas must be cooled in order for the condensation of water to start. According to the vapor pressure curve of water, there is a direct relationship between the dew point temperature and the absolute humidity, this being described in the literature by means of functions of various degrees of accuracy (e.g.: Sonntag [1] (Formeln verschiedener Genauigkeitsgrade zur Berechnung des Sattigungsdampfdruckes über Wasser und über Eis und ihre Anwendung auf einige praktische Feuchtmessaufgaben; Abhandlungen des Meteorologischen Dienstes der DDR, Akad. Verl. 1982), Sonntag [2] (Important New Values of the Physical Constants of 1986, Vapor Pressure Formulations Based on the ITS-90 and Psychrometer Formulae; Z. Meteorol. 70 (1990) 5, p. 340–344). The function most commonly used is the Magnus formula, which gives a direct relation between the dew point temperature $T_d [°C.]$ and the water vapour partial pressure $e [hpa]$.

$$e = e_w(T_d) = A \cdot \exp\left(\frac{m \cdot T_d}{T_n + T_d}\right) \quad (1)$$

$$T_d(e) = T_n \cdot \frac{\ln\left(\frac{e}{A}\right)}{m - \ln\left(\frac{e}{A}\right)} \quad \text{Magnus formulae}$$

wherein $A = 6.112 \quad m = 17.62 \quad T_n = 243.12$ (valid for ITS 90/Sonntag [2]

At a substantially higher pressure than atmospheric pressure (1013.25 hPa), corrections (Hyland [3] (A Correlation for the Second Interaction Virial Coefficients and Enhancement Factors for Moist Air; J. Research NBS, A. Physics and Chemistry 79A (1975), p. 551–560), Sonntag [2]) will have to be taken into account, which, however, do not change anything at the basic behavior.

From the functions for the absolute humidity, a known fact results:

While remaining above the dew point temperature, the absolute humidity does not change at a variation of the gas temperature. What does actually change is the relative humidity $h[\%r.h.]$, which is based on the ratio of water vapor partial pressure e at a dew point temperature $T_d$ to saturated partial pressure above water $e_w$ at a gas temperature T (Sonntag [1]):

$$F = \frac{e(T_d)}{e_w(T)} \quad (3)$$

By varying the gas temperature T, any desired relative humidity h may be adjusted at a given dew point temperature $T_d$. In particular, a relative humidity of 100% will result with $T = T_d$.

That basic behavior of moist air is utilized, e.g., with a dew point mirror for determining the dew point temperature by conducting the gas to be measured over a mirror surface that is cooled until dewing occurs for the first time. Dewing is determined through the change of reflexion of the mirror and the respective temperature is measured directly as the dew point temperature. Other systems have applied the same principle, detecting dewing, for instance, by means of acoustic surface waves or by a change of capacity on the surface.

In principle, that method is very accurate, yet does have some drawbacks, nevertheless. On the one hand, apparative expenditures are rather high, thus rendering systems expensive, on the other hand it involves the risk of the mirror getting contaminated, thus leading to increased measuring errors or unstable measuring results. Such problems may be partially solved by a number of measures, yet the system will become even more expensive. And the necessity of relatively short service intervals will remain at any event, thus raising operating costs.

Another way of determining the absolute humidity of air consists in measuring the relative humidity of air and the air temperature, and calculating the dew point temperature and equivalent quantities by aid of, e.g., the Magnus formula and its inverted functions.

Saturated vapor pressure $e_w$ at T: $e_w = e_w(T)$

Water vapor partial pressure e at T and relative humidity h: $e = e_w * h$

Dew point temperature $T_d$: $T_d = T_d(e)$

Capacitive humidity sensors for measuring the relative humidity of air are available on the market in various embodiments. Capacitive humidity sensors based on thin layer technique are characterized by a practically linear capacity—humidity behavior and as largely constant as possible a sensitivity within the measuring range.

That indirect method for determining the absolute humidity of air in view of the direct method by means of a dew point mirror offers the advantages of having shorter response times, involving lower risks of contamination, and being applicable even at high temperatures.

Disadvantages will be faced, in particular, during operation at a high relative humidity, i.e., during operation at a gas temperature in the vicinity (some 0.1° to 1° C.) of the dew point temperature.

This temperature range involves the risk of the capacitive sensor being covered by dew, which will lead to falsified measuring signals and drying out of the sensor at an insensitive time, during which no suitable measurement is to be expected.

Upon extended operation in the high-humidity range of h>95%, the effect of the sensor getting saturated may occur, which will be reflected by a shift of the sensor signal, thus also leading to strongly falsified measuring results.

2. Prior Art

From DE 19 513 274 A1 a method for measuring the dew point or a gas concentration has already been known, in which an indirect measuring procedure has been chosen. According to that method, a shift in the measuring range of the sensor is to be reached by externally cooling the sensor such that, in particular, at low values of the relative humidity, a high relative humidity will be measured after cooling, whereupon the measuring range in the region of the dew point each is shifted in a manner that as high a measuring accuracy as possible will be attained. The known mode of procedure requires two separate sensor units, the first of which sensor units comprises a humidity sensor and a temperature sensor, whereas the second unit, which is arranged on the actual point of measurement, merely comprises a temperature sensor. The first sensor unit is heated to a temperature above ambient temperature in order to prevent the humidity sensor from getting moist due to condensation. On the whole, the operating temperature of the humidity sensor is shifted into the optimum sensor temperature range, in particular, by using Peltier elements, the dew point of the environment being determined from the measuring result of the relative humidity of the humidity sensor and the measured temperature of the humidity sensor.

Furthermore, a humidity sensor is known from DE 39 11 812 A1, which comprises a sputtered polymer sensor layer. The sensor comprises an integrated heating means for heating, which is to compensate for the adverse effects occurring at high air humidities pointed out above. Details as to the mode of operation of the heating means are not found in that patent.

SUMMARY OF THE INVENTION

The invention aims at providing a method of the initially defined kind for a capacitive humidity sensor, which on the one hand eliminates the risk of falsification of the measuring results at an extended period of operation in the high-humidity range and the risk of a drift of the sensor signal. On the other hand, the method according to the invention, in particular, aims at rendering feasible measuring of the absolute humidity in a long-time stable and accurate manner even on the border to dewing such that subsequently also the relative humidity can be accurately measured in a long-time stable manner on the border to a 100% relative humidity.

To solve this object, the method according to the invention essentially consists in that the determination of the humidity of air until reaching the predetermined humidity limit value is effected by evaluating the value measured for the capacity of the sensor and that, upon reaching of a predetermined limit value, the temperature of the sensor is controlled to a constant capacity of the sensor by heating and is evaluated. By the fact that the measuring principle is changed upon reaching a defined predetermined humidity limit value, operation may be effected in the respectively optimum range without cooling of the sensor being required. Rather it will be sufficient within the scope of the present invention to merely effect heating of the sensor upon exceeding of a predetermined humidity limit value. Controlling the heating procedure in that case is extremely simple, since according to the invention heating is adjusted in a manner that the capacitive sensor retains its constant capacity. In detail, the combined temperature—humidity sensor thus is operated according to two different modes of operation depending on the humidity range:

a) The relative humidity is below a fixed limit humidity (e.g., $h_g$=75% r.h.):

The relative humidity is measured by the capacitive humidity sensor in the usual manner, the ambient temperature $T_A$ is measured by the temperature sensor. From these measured values, the dew point temperature and equivalent data may be calculated, for instance, by aid of the Magnus formula.

b) The relative humidity is above the limit humidity $h_g$:

The temperature sensor in that case is operated at such a high current that the substrate, and together therewith, the capacitive humidity sensor are heated to a temperature $T_s$>T due to lost heat. The heating capacity of the temperature sensor by a suitable circuit is controlled in a manner that the capacitive humidity sensor measures a constant relative humidity $h_g$. The operating circuit of the temperature sensor, therefore, is adjusted to a constant sensor capacity. From the voltage drop occurring at the temperature sensor, there follows the sensor temperature in conjunction with the operating current and thence the absolute humidity or dew point temperature to be measured, in conjunction with the constant sensor capacity adjusted.

At a temperature $T_s$ and a limit humidity $h_g$, using the Magnus formulae, there follows:

$$E = e_w(T_s) \cdot h_g$$

$$T_d = T_d(e) \qquad (4)$$

The advantage of the arrangement proposed consists in a sensor element to be produced in a cost-efficient manner, which, when operated in a- suitable way, offers the advantages of indirect dew point measurement, at the same time safely avoiding the disadvantages involved in high-humidity operation.

In a particularly advantageous manner, the method may be conducted in a manner that the temperature sensor is designed as a resistive sensor and is used as a heating element by power infeed and that the voltage drop at the resistive sensor is used for temperature measurement, thereby substantially reducing the structural expenditures of the temperature—humidity element.

In order to safely avoid dewing of the sensor, the humidity limit value must be preset accordingly. Advantageously, the method according to the invention is realized in a manner that the humidity limit value is chosen to be between 40% rel. humidity and 90% rel. humidity, preferably 75% rel. humidity.

Long-time stable measurement by means of a sensor to be produced in a cost-efficient manner may be ensured in that the sensors are arranged on a carrier of thermally conducting and electrically insulating material, such as, e.g., $Al_2O_3$, AlN, $Be_2O_3$, glass, or Si, thereby also ensuring mechanical stability and, in particular, temperature resistance during the heating procedure.

Advantageously, the configuration may be devised such that the thickness of the carrier material is chosen between 0.05 and 1 mm, thereby safeguarding short response times. In order to ensure as rapid a heating of the capacitive sensor as possible upon reaching of the humidity limit value, the configuration advantageously is such that the resistive sensor is arranged below the externally arranged capacitive sensor.

With a view to determining in a long-time stable manner the relative humidity in the high-humidity range, the mode of operation advantageously may be such that a further temperature sensor is used for detecting the gas temperature for the purpose of determining the relative humidity.

Taking into account the gas temperature $T_a$ measured, the relative humidity, by means of such an additional temperature probe, may be determined in a long-time stable manner even above the limit humidity $h_g$, using the calculation formulae mentioned in the introductory part.

DESCRIPTION OF THE DRAWINGS

In the following, the invention will be explained in more detail by way of an exemplary embodiment schematically illustrated in the drawings, wherein.

DETAILED DESCRIPTION OF A PREFERRED EMBODIMENT OF THE INVENTION

Figure 1:
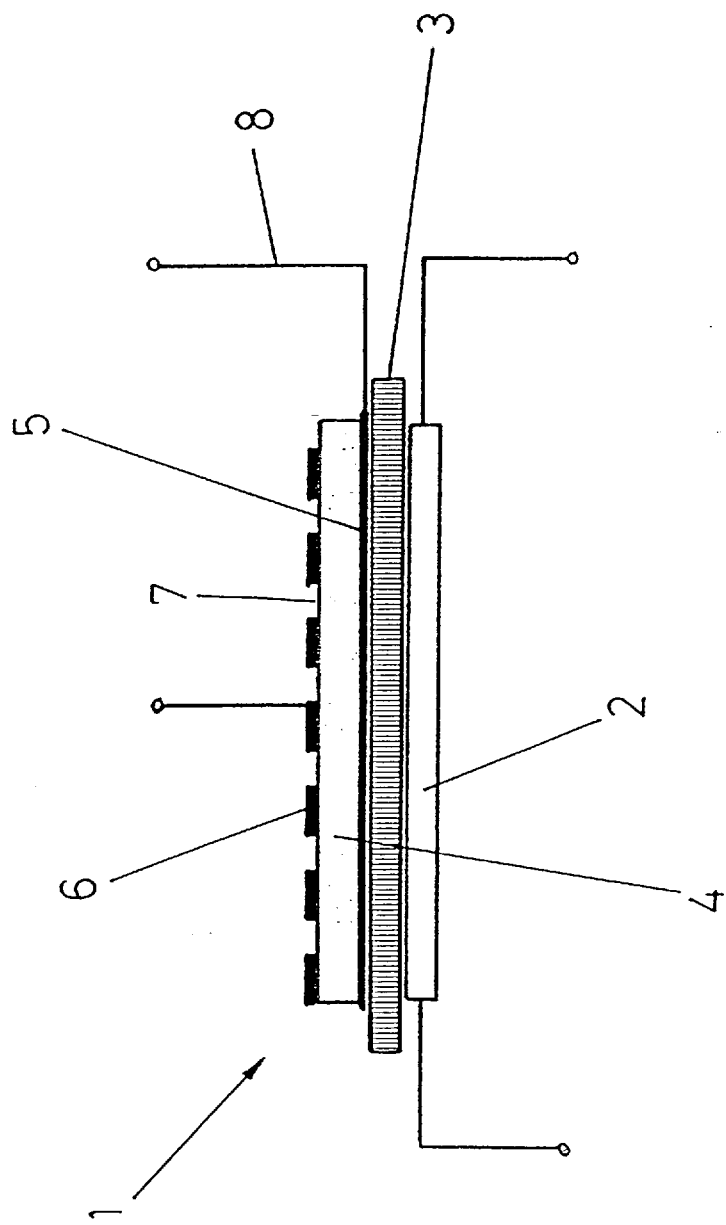
FIG. 1 illustrates a capacitive humidity sensor including a temperature probe.
Figure 2:
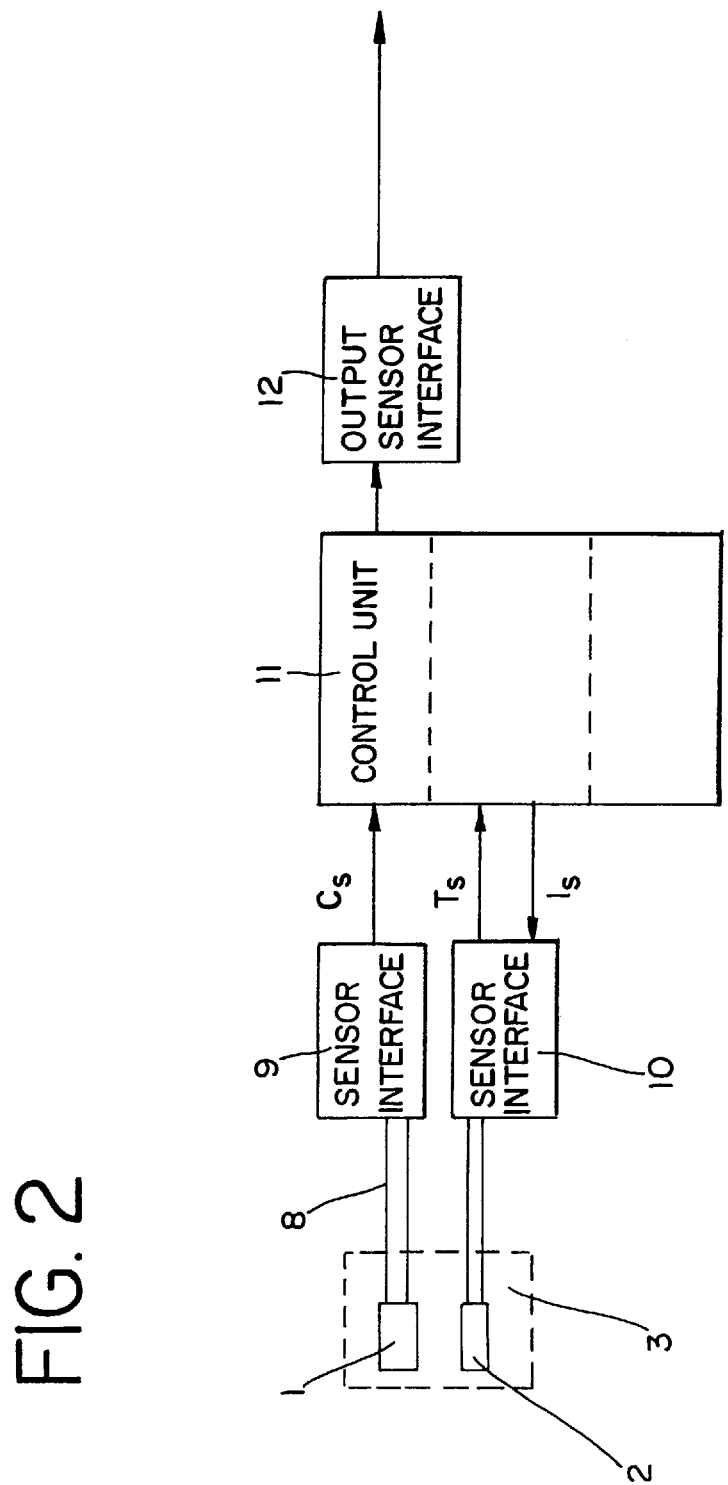
FIG. 2 illustrates an electronic circuit arrangement for measuring the absolute humidity.
Figure 3:
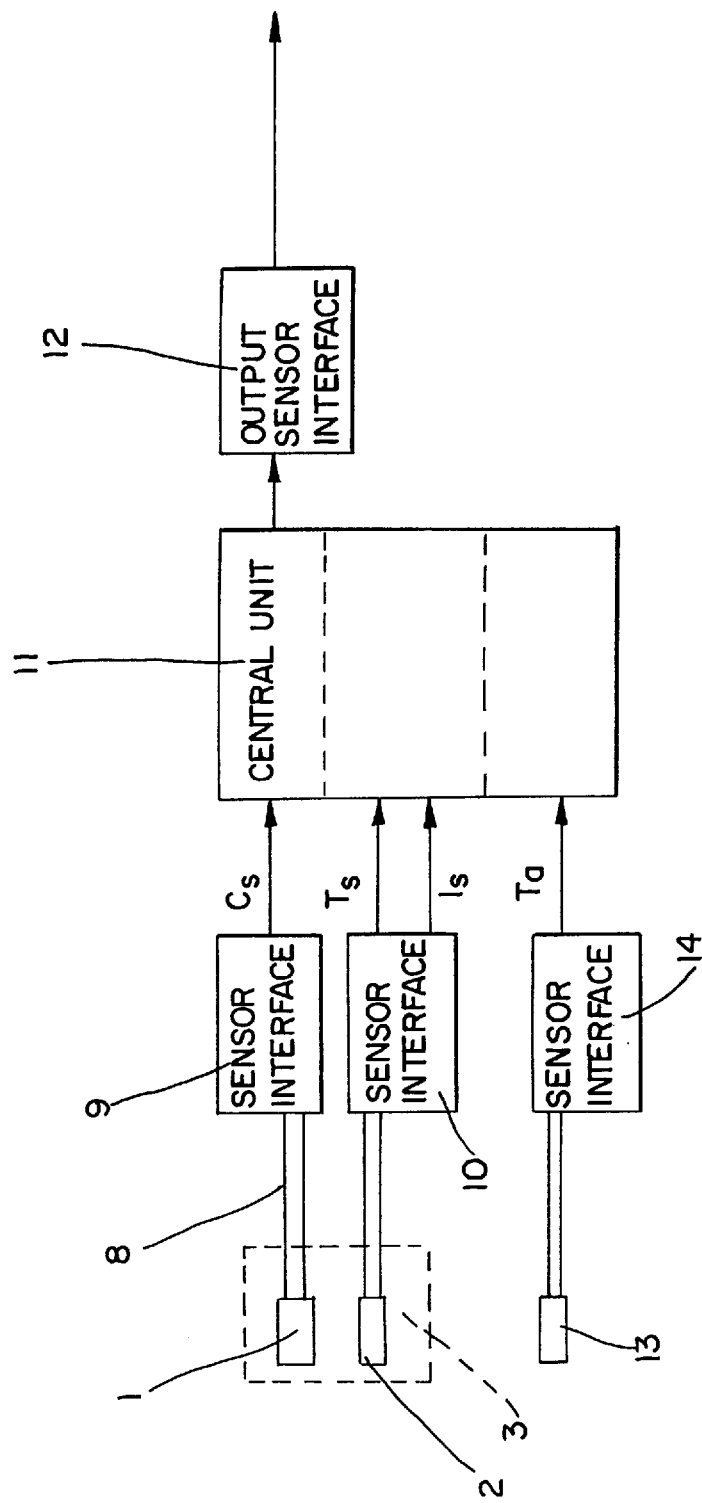
FIG. 3 illustrates an electronic circuit arrangement for measuring the relative humidity.

In FIG. 1, a capacitive humidity sensor 1 and a resistive temperature probe 2 have been applied on a thermally conductive and electrically insulating carrying body 3. The capacitive humidity sensor 1 is comprised of a humidity-absorbing dielectric 4 and two electrodes 5 and 6, wherein the electrode 6 facing away from the carrying body 3 is provided with apertures 7 or pores in order to enable air to enter the dielectric 4. The humidity sensor 1 and the temperature probe 2 by lines 8 are connected with the evaluation circuit illustrated in more detail in FIG. 2. As is apparent from FIG. 2, the output signals of the humidity sensor 1 and the temperature probe 2 are transmitted to the sensor interfaces 9 and 10 and there are converted into measured values proportional to the sensor capacity $C_s$ and to the sensor temperature $T_s$, said measured values, in turn, being input signals for a control unit 11. The sensor temperature $T_s$ is determined via the voltage drop at the temperature sensor 2, the latter operating merely as a temperature sensor at a sufficiently low sensor operating current $I_s$, without being heated. From the sensor capacity $C_s$ and from the sensor temperature $T_s$, the evaluation circuit of the control unit 11 calculates a measured value for the relative humidity. A current proportional to that measured value reaches an output signal interface 12. The relative humidity is measured at a constant temperature $T_a$ up to a preadjustable limit value of, for instance, 75%. If the relative humidity increases to above that value, the operating current $I_s$ of the temperature sensor is increased by the control circuit and the temperature sensor is heated to a temperature $T_s$ that is higher than the ambient temperature $T_a$. Consequently, the absolute humidity can be exactly determined even in the high-humidity range, since water can be prevented from condensing in the humidity sensor even in the vicinity of the dew point by increasing the sensor temperature $T_s$. In the arrangement depicted in FIG. 3, an additional temperature probe 13 is connected with the control circuit 11 via a sensor interface 14. That temperature sensor 13 enables the ambient temperature $T_a$ to be measured even in the high-humidity range, in which the sensor temperature $T_s$ is higher than the ambient temperature $T_a$ due to the temperature sensor 2 being heated. Thus, the relative humidity can be determined even in the high-humidity range owing to the simultaneous measurement of the ambient temperature $T_a$, the sensor temperature $T_s$ and the sensor capacity $C_s$.

Figure 4:
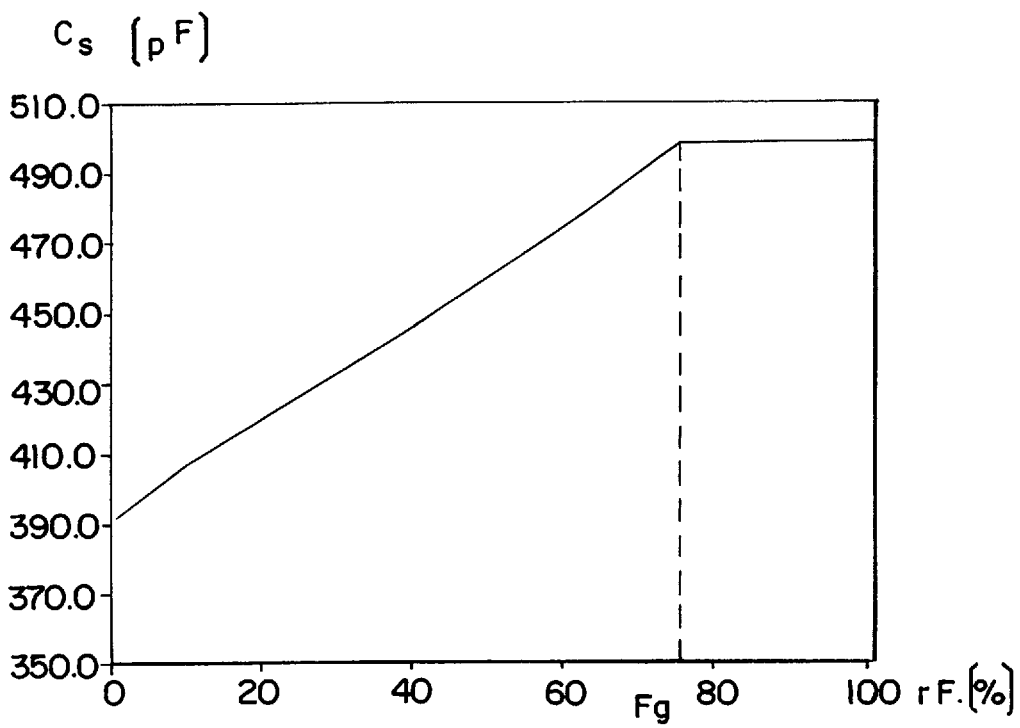
FIGS. 4 and 5 each explain the various modes of operation for measuring the humidity of air in various humidity ranges.
Figure 5:
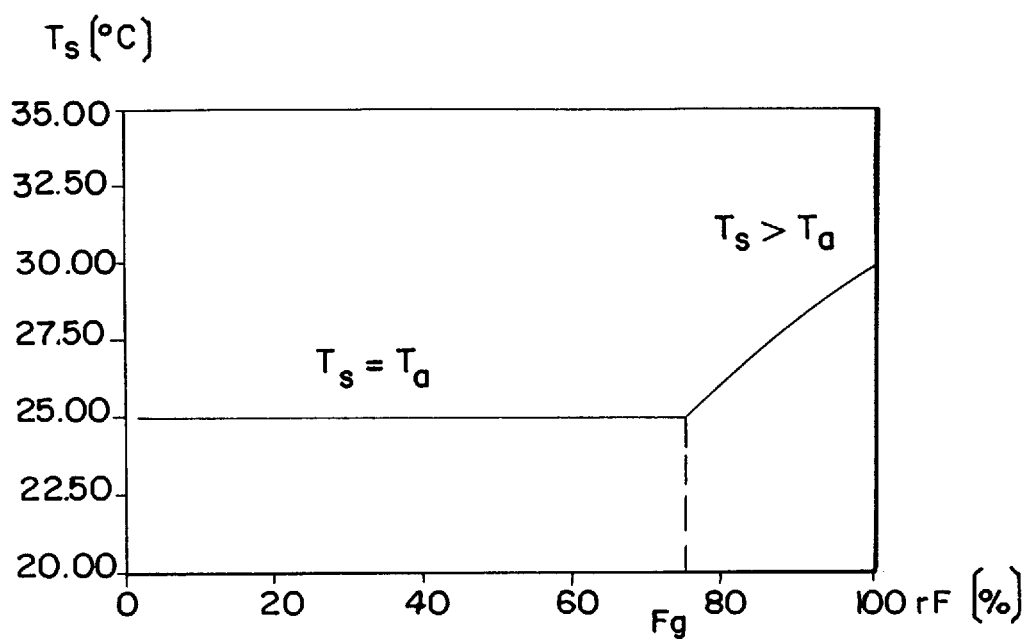

FIGS. 4 and 5 illustrate various modes of operation of the humidity sensor. The relative humidity (r.h.) in FIG. 4 has been plotted against the sensor capacity $C_s$ and in FIG. 5 against the sensor temperature $T_s$. Up to a relative humidity of 75%, the capacity of the humidity sensor is measured at a constant temperature $T_s=T_a$, as known per se, the sensor capacity $C_s$ linearly increasing with the relative humidity (r.h.). If the relative humidity (r.h.) is above the limit humidity Fg of 75%, the temperature sensor is operated with such a high current $I_s$ that the substrate, and along with it the capacitive humidity sensor, are heated to a temperature of $T_s>T_a$ due to the lost heat. In doing so, the heating performance of the temperature sensor is controlled in a manner that the capacitive humidity sensor measures a constant relative humidity, thus also a constant capacity $C_s$. Via the voltage drop at the temperature sensor, in conjunction with the operating current $I_s$, the sensor temperature Ts and hence, in conjunction with the constant capacity $C_s$ adjusted, the absolute humidity to be measured result.

What I claim is:

1. In a method for determining the absolute humidity of air by aid of a sensor means comprising a capacitive sensor and a temperature sensor as well as a heating element by providing a predetermined humidity limit value and changing the temperature of said capacitive sensor upon reaching said predetermined humidity limit value, the improvement comprising the steps of measuring the capacity of said capacitive sensor so as to obtain a capacity value, determining the humidity of air until reaching said predetermined humidity limit value by evaluating said capacity value, upon reaching said predetermined humidity limit value, controlling the temperature of said sensor means so as to maintain a constant capacity value of said capacitive sensor by heating said capacitive sensor, and evaluating said temperature.

2. A method as set forth in claim 1, wherein said temperature sensor is constructed as a resistive sensor and is used as said heating element by power infeed, and wherein said resistive sensor experiences a voltage drop and said voltage drop is applied for temperature measuring.

3. A method as set forth in claim 1, wherein said humidity limit value is chosen to range between 40% relative humidity and 90% relative humidity.

4. A method as set forth in claim 3, wherein said humidity limit value is chosen to be 75% relative humidity.

5. A method as set forth in claim 1, further providing a carrier means made of thermally conducting and electrically insulating material for arranging said sensor means thereon.

6. A method as set forth in claim 5, wherein said thermally conducting and electrically insulating material is selected from the group consisting of $Al_2O_3$, AlN, $Be_2O_3$, glass, and Si.

7. A method as set forth in claim 5, wherein said carrying means has a thickness ranging between 0.05 mm and 1 mm.

8. A method as set forth in claim 1, wherein said temperature sensor is arranged below said capacitive sensor located externally.

9. A method as set forth in claim 1, further using an additional temperature sensor for gas temperature detection with a view to determining said relative humidity.

* * * * *

UNITED STATES PATENT AND TRADEMARK OFFICE
CERTIFICATE OF CORRECTION

PATENT NO. : 5,814,726
DATED : September 29, 1998
INVENTOR(S) : Helmut Mitter

It is certified that error appears in the above-identified patent and that said Letters Patent is hereby corrected as shown below:

On the Title Page

In column 1, before line 1, under "U.S. PATENT DOCUMENTS", please insert the following:

--4,482,882    11/1984    Lüder et al.    338/34--.

In column 1, after line 2, under "FOREIGN PATENT DOCUMENTS", please insert the following:

--2851686    6/1979    Germany--.

Signed and Sealed this

Twenty-sixth Day of December, 2000

Attest:

Q. TODD DICKINSON

*Attesting Officer*      *Director of Patents and Trademarks*